(12) United States Patent
Reicher

(10) Patent No.: US 9,092,727 B1
(45) Date of Patent: Jul. 28, 2015

(54) EXAM TYPE MAPPING

(75) Inventor: Murray A. Reicher, Rancho Santa Fe, CA (US)

(73) Assignee: D.R. Systems, Inc., San Diego, CA (US)

( * ) Notice: Subject to any disclaimer, the term of this patent is extended or adjusted under 35 U.S.C. 154(b) by 255 days.

(21) Appl. No.: 13/572,552

(22) Filed: Aug. 10, 2012

Related U.S. Application Data

(60) Provisional application No. 61/522,633, filed on Aug. 11, 2011.

(51) Int. Cl.
*G06N 5/02* (2006.01)

(52) U.S. Cl.
CPC ........................................ *G06N 5/02* (2013.01)

(58) Field of Classification Search
None
See application file for complete search history.

(56) References Cited

U.S. PATENT DOCUMENTS

| | | | |
|---|---|---|---|
| 4,672,683 A | 6/1987 | Matsueda | |
| 5,123,056 A | 6/1992 | Wilson | |
| 5,179,651 A | 1/1993 | Taaffe et al. | |
| 5,431,161 A | 7/1995 | Ryals et al. | |
| 5,452,416 A | 9/1995 | Hilton et al. | |
| 5,542,003 A | 7/1996 | Wofford | |
| 5,734,915 A | 3/1998 | Roewer | |
| 5,740,267 A | 4/1998 | Echerer et al. | |
| 5,779,634 A | 7/1998 | Ema et al. | |
| 5,852,646 A | 12/1998 | Klotz et al. | |
| 5,926,568 A | 7/1999 | Chaney et al. | |
| 5,954,650 A | 9/1999 | Saito et al. | |
| 5,976,088 A | 11/1999 | Urbano et al. | |
| 5,986,662 A | 11/1999 | Argiro et al. | |
| 5,987,345 A | 11/1999 | Engelmann et al. | |
| 5,995,644 A | 11/1999 | Lai et al. | |
| 6,115,486 A | 9/2000 | Cantoni | |
| 6,128,002 A | 10/2000 | Leiper | |
| 6,151,581 A | 11/2000 | Kraftson et al. | |
| 6,175,643 B1 | 1/2001 | Lai et al. | |
| 6,177,937 B1 | 1/2001 | Stockham et al. | |
| 6,185,320 B1 | 2/2001 | Bick et al. | |
| 6,243,095 B1 | 6/2001 | Shile et al. | |
| 6,269,379 B1 | 7/2001 | Hiyama et al. | |
| 6,304,667 B1 | 10/2001 | Reitano | |
| 6,347,329 B1 | 2/2002 | Evans | |
| 6,351,547 B1 | 2/2002 | Johnson et al. | |
| 6,383,135 B1 | 5/2002 | Chikovani et al. | |
| 6,388,687 B1 | 5/2002 | Brackett et al. | |
| 6,424,996 B1 | 7/2002 | Killcommons et al. | |
| 6,438,533 B1 | 8/2002 | Spackman et al. | |
| 6,463,169 B1 | 10/2002 | Ino et al. | |
| 6,532,299 B1 | 3/2003 | Sachdeva et al. | |

(Continued)

FOREIGN PATENT DOCUMENTS

WO WO 2007/131157 11/2007

OTHER PUBLICATIONS

Interview Summary, dated Mar. 4, 2015 in U.S. Appl. No. 11/942,687.

(Continued)

*Primary Examiner* — Kakali Chaki
*Assistant Examiner* — Kevin W Figueroa
(74) *Attorney, Agent, or Firm* — Knobbe, Martens, Olson & Bear LLP

(57) ABSTRACT

Provided herein are various systems and methods of using an exam type data structure to map exam types in various formats to master exam types that may be associated with customized rules or other features.

27 Claims, 9 Drawing Sheets

(56) References Cited

U.S. PATENT DOCUMENTS

| | | |
|---|---|---|
| 6,532,311 B1 | 3/2003 | Pritt |
| 6,556,695 B1 | 4/2003 | Packer et al. |
| 6,556,724 B1 | 4/2003 | Chang et al. |
| 6,563,950 B1 | 5/2003 | Wiskott et al. |
| 6,574,629 B1 | 6/2003 | Kaufman et al. |
| 6,577,753 B2 | 6/2003 | Ogawa |
| 6,603,494 B1 | 8/2003 | Banks et al. |
| 6,606,171 B1 | 8/2003 | Renk et al. |
| 6,618,060 B1 | 9/2003 | Brackett |
| 6,630,937 B2 | 10/2003 | Kallergi et al. |
| 6,678,764 B2 | 1/2004 | Parvulescu et al. |
| 6,697,067 B1 | 2/2004 | Callahan et al. |
| 6,697,506 B1 | 2/2004 | Oian et al. |
| 6,734,880 B2 | 5/2004 | Chang et al. |
| 6,760,755 B1 | 7/2004 | Brackett |
| 6,775,402 B2 | 8/2004 | Bacus et al. |
| 6,778,689 B1 | 8/2004 | Aksit et al. |
| 6,820,093 B2 | 11/2004 | de la Huerga |
| 6,820,100 B2 | 11/2004 | Funahashi |
| 6,829,377 B2 | 12/2004 | Milioto |
| 6,864,794 B2 | 3/2005 | Betz |
| 6,886,133 B2 | 4/2005 | Bailey et al. |
| 6,891,920 B1 | 5/2005 | Minyard et al. |
| 6,894,707 B2 | 5/2005 | Nemoto |
| 6,909,436 B1 | 6/2005 | Pianykh et al. |
| 6,909,795 B2 | 6/2005 | Tecotzky et al. |
| 6,917,696 B2 | 7/2005 | Soenksen |
| 6,988,075 B1 | 1/2006 | Hacker |
| 6,996,205 B2 | 2/2006 | Capolunghi et al. |
| 7,016,952 B2 | 3/2006 | Mullen et al. |
| 7,022,073 B2 | 4/2006 | Fan et al. |
| 7,027,633 B2 | 4/2006 | Foran et al. |
| 7,031,846 B2 | 4/2006 | Kaushikkar et al. |
| 7,043,474 B2 | 5/2006 | Mojsilovic |
| 7,050,620 B2 | 5/2006 | Heckman |
| 7,054,473 B1 | 5/2006 | Roehrig et al. |
| 7,058,901 B1 | 6/2006 | Hafey et al. |
| 7,092,572 B2 | 8/2006 | Huang et al. |
| 7,103,205 B2 | 9/2006 | Wang et al. |
| 7,106,479 B2 | 9/2006 | Roy et al. |
| 7,110,616 B2 | 9/2006 | Ditt et al. |
| 7,113,186 B2 | 9/2006 | Kim et al. |
| 7,139,416 B2 | 11/2006 | Vuylsteke |
| 7,149,334 B2 | 12/2006 | Dehmeshki |
| 7,155,043 B2 | 12/2006 | Daw |
| 7,162,623 B2 | 1/2007 | Yngvesson |
| 7,170,532 B2 | 1/2007 | Sako |
| 7,174,054 B2 | 2/2007 | Manber et al. |
| 7,209,149 B2 | 4/2007 | Jogo |
| 7,212,661 B2 | 5/2007 | Samara et al. |
| 7,218,763 B2 | 5/2007 | Belykh et al. |
| 7,224,852 B2 | 5/2007 | Lipton et al. |
| 7,260,249 B2 | 8/2007 | Smith |
| 7,263,710 B1 | 8/2007 | Hummell et al. |
| 7,272,610 B2 | 9/2007 | Torres |
| 7,346,199 B2 | 3/2008 | Pfaff |
| 7,366,992 B2 | 4/2008 | Thomas, III |
| 7,412,111 B2 | 8/2008 | Battle et al. |
| 7,450,747 B2 | 11/2008 | Jabri et al. |
| 7,505,782 B2 | 3/2009 | Chu |
| 7,526,114 B2 | 4/2009 | Seul et al. |
| 7,526,132 B2 | 4/2009 | Koenig |
| 7,545,965 B2 | 6/2009 | Suzuki et al. |
| 7,583,861 B2 | 9/2009 | Hanna et al. |
| 7,613,335 B2 | 11/2009 | McLennan et al. |
| 7,634,121 B2 | 12/2009 | Novatzky et al. |
| 7,636,413 B2 | 12/2009 | Toth |
| 7,656,543 B2 | 2/2010 | Atkins |
| 7,660,488 B2 | 2/2010 | Reicher et al. |
| 7,668,352 B2 | 2/2010 | Tecotzky et al. |
| 7,683,909 B2 | 3/2010 | Takekoshi |
| 7,698,152 B2 | 4/2010 | Reid |
| 7,716,277 B2 | 5/2010 | Yamatake |
| 7,787,672 B2 | 8/2010 | Reicher et al. |
| 7,834,891 B2 | 11/2010 | Yarger et al. |
| 7,885,440 B2 | 2/2011 | Fram et al. |
| 7,920,152 B2 | 4/2011 | Fram et al. |
| 7,953,614 B1 | 5/2011 | Reicher |
| 7,970,625 B2 | 6/2011 | Reicher et al. |
| 8,019,138 B2 | 9/2011 | Reicher et al. |
| 8,046,044 B2 | 10/2011 | Stazzone et al. |
| 8,050,938 B1 | 11/2011 | Green, Jr. et al. |
| 8,065,166 B2 | 11/2011 | Maresh et al. |
| 8,094,901 B1 | 1/2012 | Reicher et al. |
| 8,217,966 B2 | 7/2012 | Fram et al. |
| 8,244,014 B2 | 8/2012 | Reicher et al. |
| 8,292,811 B2 | 10/2012 | Relkuntwar et al. |
| 8,379,051 B2 | 2/2013 | Brown |
| 8,380,533 B2 | 2/2013 | Reicher et al. |
| 8,391,643 B2 | 3/2013 | Melbourne et al. |
| 8,406,491 B2 | 3/2013 | Gee et al. |
| 8,457,990 B1 | 6/2013 | Reicher et al. |
| 8,554,576 B1 | 10/2013 | Reicher et al. |
| 8,560,050 B2 | 10/2013 | Martin et al. |
| 8,610,746 B2 | 12/2013 | Fram et al. |
| 8,626,527 B1 | 1/2014 | Reicher et al. |
| 8,693,757 B2 | 4/2014 | Gundel |
| 8,712,120 B1 | 4/2014 | Reicher et al. |
| 8,731,259 B2 | 5/2014 | Reicher et al. |
| 8,751,268 B1 | 6/2014 | Reicher et al. |
| 8,879,807 B2 | 11/2014 | Fram et al. |
| 8,913,808 B2 | 12/2014 | Reicher et al. |
| 9,042,617 B1 | 5/2015 | Reicher et al. |
| 2001/0016822 A1 | 8/2001 | Bessette |
| 2001/0042124 A1 | 11/2001 | Barron |
| 2002/0016718 A1 | 2/2002 | Rothschild et al. |
| 2002/0021828 A1 | 2/2002 | Papier et al. |
| 2002/0039084 A1 | 4/2002 | Yamaguchi |
| 2002/0044696 A1 | 4/2002 | Sirohey et al. |
| 2002/0073429 A1 | 6/2002 | Beane et al. |
| 2002/0090124 A1 | 7/2002 | Soubelet et al. |
| 2002/0091659 A1 | 7/2002 | Beaulieu et al. |
| 2002/0103673 A1 | 8/2002 | Atwood |
| 2002/0103827 A1 | 8/2002 | Sesek |
| 2002/0110285 A1 | 8/2002 | Wang et al. |
| 2002/0180883 A1 | 12/2002 | Tomizawa et al. |
| 2003/0005464 A1 | 1/2003 | Gropper et al. |
| 2003/0016850 A1 | 1/2003 | Kaufman et al. |
| 2003/0028402 A1 | 2/2003 | Ulrich et al. |
| 2003/0037054 A1 | 2/2003 | Dutta et al. |
| 2003/0065613 A1 | 4/2003 | Smith |
| 2003/0071829 A1 | 4/2003 | Bodicker et al. |
| 2003/0101291 A1 | 5/2003 | Mussack et al. |
| 2003/0115083 A1 | 6/2003 | Masarie et al. |
| 2003/0120516 A1 | 6/2003 | Perednia |
| 2003/0140141 A1 | 7/2003 | Mullen et al. |
| 2003/0160095 A1 | 8/2003 | Segal |
| 2003/0164860 A1 | 9/2003 | Shen et al. |
| 2003/0184778 A1 | 10/2003 | Chiba |
| 2003/0187689 A1 | 10/2003 | Barnes et al. |
| 2003/0190062 A1 | 10/2003 | Noro et al. |
| 2003/0204420 A1 | 10/2003 | Wilkes et al. |
| 2003/0215122 A1 | 11/2003 | Tanaka |
| 2004/0024303 A1 | 2/2004 | Banks et al. |
| 2004/0086163 A1 | 5/2004 | Moriyama et al. |
| 2004/0088192 A1 | 5/2004 | Schmidt et al. |
| 2004/0105574 A1 | 6/2004 | Pfaff |
| 2004/0114714 A1 | 6/2004 | Minyard et al. |
| 2004/0143582 A1 | 7/2004 | Vu |
| 2004/0161164 A1 | 8/2004 | Dewaele |
| 2004/0165791 A1 | 8/2004 | Kaltanji |
| 2004/0172306 A1 | 9/2004 | Wohl et al. |
| 2004/0174429 A1 | 9/2004 | Chu |
| 2004/0190780 A1 | 9/2004 | Shiibashi et al. |
| 2004/0202387 A1 | 10/2004 | Yngvesson |
| 2004/0243435 A1 | 12/2004 | Williams |
| 2004/0252871 A1 | 12/2004 | Tecotzky et al. |
| 2004/0254816 A1 | 12/2004 | Myers |
| 2004/0255252 A1 | 12/2004 | Rodriguez et al. |
| 2005/0010531 A1 | 1/2005 | Kushalnagar et al. |
| 2005/0027569 A1 | 2/2005 | Gollogly et al. |
| 2005/0027570 A1 | 2/2005 | Maier et al. |
| 2005/0043970 A1 | 2/2005 | Hsieh |
| 2005/0063575 A1 | 3/2005 | Ma et al. |

(56) References Cited

U.S. PATENT DOCUMENTS

| | | | |
|---|---|---|---|
| 2005/0065424 A1 | 3/2005 | Shah et al. | |
| 2005/0074157 A1 | 4/2005 | Thomas, III | |
| 2005/0075544 A1 | 4/2005 | Shapiro et al. | |
| 2005/0088534 A1 | 4/2005 | Shen et al. | |
| 2005/0107689 A1 | 5/2005 | Sasano | |
| 2005/0108058 A1 | 5/2005 | Weidner et al. | |
| 2005/0113681 A1 | 5/2005 | DeFreitas et al. | |
| 2005/0114178 A1 | 5/2005 | Krishnamurthy et al. | |
| 2005/0114179 A1 | 5/2005 | Brackett et al. | |
| 2005/0114283 A1 | 5/2005 | Pearson et al. | |
| 2005/0184988 A1 | 8/2005 | Yanof et al. | |
| 2005/0197860 A1 | 9/2005 | Joffe et al. | |
| 2005/0238218 A1 | 10/2005 | Nakamura | |
| 2005/0244041 A1 | 11/2005 | Tecotzky et al. | |
| 2005/0273009 A1 | 12/2005 | Deischinger et al. | |
| 2006/0008181 A1 | 1/2006 | Takekoshi | |
| 2006/0031097 A1 | 2/2006 | Lipscher et al. | |
| 2006/0050152 A1 | 3/2006 | Rai et al. | |
| 2006/0058603 A1 | 3/2006 | Dave et al. | |
| 2006/0095426 A1 | 5/2006 | Takachio et al. | |
| 2006/0111941 A1 | 5/2006 | Blom | |
| 2006/0171574 A1 | 8/2006 | DelMonego et al. | |
| 2006/0181548 A1 | 8/2006 | Hafey | |
| 2006/0230072 A1 | 10/2006 | Partovi et al. | |
| 2006/0241979 A1 | 10/2006 | Sato et al. | |
| 2006/0277075 A1 | 12/2006 | Salwan | |
| 2006/0282408 A1 | 12/2006 | Wisely et al. | |
| 2007/0050701 A1 | 3/2007 | El Emam et al. | |
| 2007/0055550 A1 | 3/2007 | Courtney et al. | |
| 2007/0064984 A1 | 3/2007 | Vassa et al. | |
| 2007/0067124 A1 | 3/2007 | Kimpe et al. | |
| 2007/0073556 A1 | 3/2007 | Lau et al. | |
| 2007/0106535 A1 | 5/2007 | Matsunaga | |
| 2007/0106633 A1 | 5/2007 | Reiner | |
| 2007/0109402 A1 | 5/2007 | Niwa | |
| 2007/0124541 A1 | 5/2007 | Lang et al. | |
| 2007/0159962 A1 | 7/2007 | Mathavu et al. | |
| 2007/0162308 A1 | 7/2007 | Peters | |
| 2007/0174079 A1 | 7/2007 | Kraus | |
| 2007/0192140 A1 | 8/2007 | Gropper | |
| 2007/0239481 A1 | 10/2007 | DiSilvestro et al. | |
| 2008/0016111 A1 | 1/2008 | Keen | |
| 2008/0059245 A1 | 3/2008 | Sakaida et al. | |
| 2008/0100612 A1 | 5/2008 | Dastmalchi et al. | |
| 2008/0103828 A1 | 5/2008 | Squilla et al. | |
| 2008/0125846 A1 | 5/2008 | Battle et al. | |
| 2008/0126982 A1 | 5/2008 | Sadikali et al. | |
| 2008/0136838 A1 | 6/2008 | Goede et al. | |
| 2008/0275913 A1* | 11/2008 | van Arragon et al. | 707/104.1 |
| 2008/0279439 A1 | 11/2008 | Minyard et al. | |
| 2009/0028410 A1 | 1/2009 | Shimazaki | |
| 2009/0080719 A1 | 3/2009 | Watt | |
| 2009/0123052 A1 | 5/2009 | Ruth et al. | |
| 2009/0129643 A1 | 5/2009 | Natanzon et al. | |
| 2009/0132586 A1 | 5/2009 | Napora et al. | |
| 2009/0150481 A1 | 6/2009 | Garcia et al. | |
| 2009/0182577 A1 | 7/2009 | Squilla et al. | |
| 2009/0198514 A1 | 8/2009 | Rhodes | |
| 2009/0213034 A1 | 8/2009 | Wu et al. | |
| 2009/0248442 A1* | 10/2009 | Pacheco et al. | 705/3 |
| 2009/0268986 A1 | 10/2009 | Holstein et al. | |
| 2010/0053353 A1 | 3/2010 | Hunter et al. | |
| 2010/0138239 A1* | 6/2010 | Reicher et al. | 705/3 |
| 2010/0198608 A1 | 8/2010 | Kaboff et al. | |
| 2010/0211409 A1 | 8/2010 | Kotula et al. | |
| 2010/0246981 A1 | 9/2010 | Hu et al. | |
| 2010/0299157 A1 | 11/2010 | Fram et al. | |
| 2011/0016430 A1 | 1/2011 | Fram | |
| 2011/0110572 A1 | 5/2011 | Guehring et al. | |
| 2011/0316873 A1 | 12/2011 | Reicher | |
| 2012/0130729 A1* | 5/2012 | Raizada et al. | 705/2 |
| 2012/0163684 A1 | 6/2012 | Natanzon et al. | |
| 2013/0083023 A1 | 4/2013 | Fram | |
| 2013/0159019 A1 | 6/2013 | Reicher | |

OTHER PUBLICATIONS

Final Office Action dated Apr. 1, 2015 in U.S. Appl. No. 14/043,165.
Office Action dated Mar. 17, 2015 in U.S. Appl. No. 13/768,765.
Notice of Allowance dated Mar. 19, 2015, 2015 in U.S. Appl. No. 13/572,397.
Notice of Allowance, dated Mar. 3, 2015 in U.S. Appl. No. 13/572,547.
Corrected Notice of Allowance, dated Apr. 10, 2015 in U.S. Appl. No. 13/572,547.
Office Action dated Mar. 3, 2015 in U.S. Appl. No. 14/095,123.
U.S. Appl. No. 12/437,522, filed May 7, 2009, Fram.
U.S. Appl. No. 13/572,397, filed Aug. 10, 2012, Reicher.
U.S. Appl. No. 13/572,547, filed Aug. 10, 2012, Reicher.
Non-Final Office Action dated Aug. 28, 2007 in U.S. Appl. No. 11/179,384.
Final Office Action dated Jun. 26, 2008 in U.S. Appl. No. 11/179,384.
Non-Final Office Action dated Dec. 29, 2008 in U.S. Appl. No. 11/179,384.
Final Office Action dated Jul. 24, 2009, in U.S. Appl. No. 11/179,384.
Notice of Allowance dated Nov. 3, 2009, in U.S. Appl. No. 11/179,384.
Non-Final Office Action dated Aug. 18, 2010 in U.S. Appl. No. 12/702,976.
Interview Summary dated Dec. 1, 2010, in U.S. Appl. No. 12/702,976.
Final Office Action dated Feb. 17, 2011 in U.S. Appl. No. 12/702,976.
Office Action dated Dec. 11, 2013, in U.S. Appl. No. 13/477,853.
Final Office Action dated Jun. 13, 2014, in U.S. Appl. No. 13/477,853.
Notice of Allowance dated Aug. 15, 2014, in U.S. Appl. No. 13/477,853.
Non-Final Office Action dated Oct. 1, 2009, in U.S. Appl. No. 11/268,261.
Notice of Allowance dated Feb. 2, 2010, in U.S. Appl. No. 11/268,261.
Interview Summary dated Jan. 25, 2010, in U.S. Appl. No. 11/268,261.
Notice of Allowance dated Oct. 8, 2010, in U.S. Appl. No. 11/268,261.
Notice of Allowance dated Dec. 3, 2010, in U.S. Appl. No. 11/268,261.
Notice of Allowance dated Jan. 6, 2011, in U.S. Appl. No. 11/268,261.
Notice of Allowance dated Jul. 3, 2014, in U.S. Appl. No. 12/857,915.
"Corrected" Notice of Allowance dated Aug. 15, 2014, in U.S. Appl. No. 12/857,915.
Non-Final Office Action dated May 13, 2009, in U.S. Appl. No. 11/265,979.
Final Office Action dated Dec. 22, 2009 in U.S. Appl. No. 11/265,979.
Non-Final Office Action dated Jul. 8, 2010 in U.S. Appl. No. 11/265,979.
Interview Summary dated Mar. 4, 2010 in U.S. Appl. No. 11/265,979.
Interview Summary dated Nov. 16, 2010 in U.S. Appl. No. 11/265,979.
Final Office Action dated Dec. 23, 2010 in U.S. Appl. No. 11/265,979.
Interview Summary dated Mar. 17, 2011 in U.S. Appl. No. 11/265,979.
Non-Final Office Action dated Aug. 24, 2009 in U.S. Appl. No. 11/268,262.
Non-Final Office Action dated Apr. 16, 2010 in U.S. Appl. No. 11/268,262.
Interview Summary dated Nov. 24, 2009 in U.S. Appl. No. 11/268,262.
Interview Summary dated May 12, 2010 in U.S. Appl. No. 11/268,262.
Final Office Action dated Oct. 28, 2010 in U.S. Appl. No. 11/268,262.
Interview Summary dated Dec. 1, 2010 in U.S. Appl. No. 11/268,262.
Notice of Allowance dated Dec. 1, 2010 in U.S. Appl. No. 11/268,262.
Notice of Allowance dated Feb. 25, 2011 in U.S. Appl. No. 11/268,262.

(56) References Cited

OTHER PUBLICATIONS

Non-Final Office Action dated Jul. 27, 2009 in U.S. Appl. No. 11/265,978.
Notice of Allowance dated Nov. 19, 2009 in U.S. Appl. No. 11/265,978.
Notice of Allowance dated Apr. 19, 2010 in U.S. Appl. No. 11/265,978.
Supplemental Notice of Allowance dated May 3, 2010 in U.S. Appl. No. 11/265,978.
Supplemental Notice of Allowance dated Aug. 3, 2010 in U.S. Appl. No. 11/265,978.
Non-Final Office Action dated May 26, 2010 in U.S. Appl. No. 11/942,674.
Interview Summary dated Jul. 26, 2010 in U.S. Appl. No. 11/942,674.
Final Office Action dated Nov. 26, 2010 in U.S. Appl. No. 11/942,674.
Interview Summary dated Mar. 2, 2011 in U.S. Appl. No. 11/942,674.
Notice of Allowance, dated Apr. 1, 2011 in U.S. Application No. 11/942,674.
Non Final Office Action dated Sep. 16, 2010 in U.S. Appl. No. 11/942,687.
Interview Summary dated Dec. 3, 2010 in U.S. Appl. No. 11/942,687.
Final Office Action, dated Apr. 5, 2011 in U.S. Appl. No. 11/942,687.
Interview Summary, dated Jun. 17, 2014 in U.S. Appl. No. 11/942,687.
Office Action, dated Jul. 18, 2014 in U.S. Appl. No. 11/942,687.
Non-Final Office Action dated Apr. 14, 2010 in U.S. Appl. No. 11/944,027.
Interview Summary dated May 13, 2010 in U.S. Appl. No. 11/944,027.
Final Office Action dated Dec. 23, 2010 in U.S. Appl. No. 11/944,027.
Interview Summary dated Mar. 31, 2011 in U.S. Appl. No. 11/944,027.
Office Action dated Apr. 19, 2012 in U.S. Appl. No. 11/944,027.
Non-Final Office Action dated Sep. 29, 2010 in U.S. Appl. No. 11/944,000.
Final Office Action dated Apr. 20, 2011 in U.S. Appl. No. 11/944,000.
Office Action dated Sep. 11, 2014 in U.S. Appl. No. 14/179,328.
Notice of Allowance dated Jan. 14, 2015 in U.S. Appl. No. 14/179,328.
Office Action dated Jun. 27, 2014 in U.S. Appl. No. 13/572,397.
Final Office Action dated Jan. 13, 2015 in U.S. Appl. No. 13/572,397.
Office Action dated Aug. 6, 2014 in U.S. Appl. No. 13/572,547.
AGFA HealthCare, color brochure "IMPAX 6: Digital Image and Information Management," © 2012 Agfa HealthCare N.V. Downloaded from http://www.agfahealthcare.com/global/en/he/library/libraryopen?ID=32882925. Accessed on Feb. 9, 2015.
AGFA HealthCare, IMPAX 6.5 Datasheet (US)2012. © 2012 Agfa HealthCare N.V. Downloaded from http://www.agfahealthcare.com/global/en/he/library/libraryopen?ID=37459801. Accessed on Feb. 9, 2015.
AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.
ASPYRA's Imaging Solutions, 3 page color print out. Accessed at http://www.aspyra.com/imaging-solutions. Accessed on Feb. 9, 2015.
AVREO, interWorks—RIS/PACS package, 2 page color brochure, © 2014, Avreo, Inc. (Document MR-5032 Rev. 4). Downloaded from http://www.avreo.com/ProductBrochures/MR-5032Rev.%204interWORKS%20RISPACSPackage.pdf. Accessed on Feb. 9, 2015.
BRIT Systems, BRIT PACS View Viewer, 2 page color brochure, (BPB-BPV-0001). Downloaded from http://www.brit.com/pdfs/britpacsview.pdf. Accessed on Feb. 9, 2015.
BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.
BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.
CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.
Carestream, Cardiology PACS, 8 page color brochure. (CAT 866 6075 06/12). © Carestream Health, Inc., 2012. Downloaded from http://www.carestream.com/cardioPACS_brochure_M1-877.pdf. Accessed on Feb. 9, 2015.
Carestream, Vue PACS, 8 page color brochure. (CAT 300 1035 5/14). © Carestream Health, Inc., 2014. Downloaded from http://www.carestream.com/csPACS_brochure_M1-876.pdf. Accessed on Feb. 9, 2015.
Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.
CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.
Crowley, Rebecca et al., Development of Visual Diagnostic Expertise in Pathology: an Information-processing Study, Jan. 2003, Journal of the American medical Informatics Association, vol. 10, No. 1, pp. 39-51.
DR Systems, Dominator™ Guide for Reading Physicians, Release 8.2, 546 pages, (TCP-000260-A), © 1997-2009, DR Systems, Inc. Downloaded from https://resources.dominator.com/assets/004/6999.pdf. Document accessed Feb. 9, 2015.
DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015.
Erickson, et al.: "Effect of Automated Image Registration on Radiologist Interpretation," Journal of Digital Imaging, vol. 20, No. 2 Jun. 2007; pp. 105-113.
Erickson, et al.: "Image Registration Improves Confidence and Accuracy of Image Interpretation," Special Issue-Imaging Informatics, Cancer Informatics 2007:1 19-24.
FUJIFILM Medical Systems, SYNAPSE® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.
FUJIFILM Medical Systems, SYNAPSE® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.
FUJIFILM Medical Systems, SYNAPSE® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.
GE Healthcare, Centricity PACS, in 8 page printout. Accessed at http://www3.gehealthcare.com/en/products/categories/healthcare_it/medical_imaging_informatics_-_ris-pacs-cvis/centricity_pacs. Accessed on Feb. 9, 2015.
Handylife.com—Overview of Handy Patients Enterprise, in 2 page printout. Accessed from http://www.handylife.com/en/software/overview.html. Accessed on Feb. 18, 2015.
Handylife.com—Features of Handy Patients Enterprise, in 4 page printout. Accessed from http://www.handylife.com/en/software/features.html. Accessed on Feb. 18, 2015.

(56) References Cited

OTHER PUBLICATIONS

Handylife.com—Screenshots of Handy Patients Enterprise, in 2 page printout. Accessed from http://www.handylife.com/en/software/screenshots.html. Accessed on Feb. 18, 2015.
iCRco, I See the Future, in 12 page., color brochure, (BR080809AUS), © 2009 iCRco.ClarityPACS. Downloaded from http://www.claritypacs.com/pdfs/ISeeFuture_26_Web.pdf. Accessed on Feb. 9, 2015.
Imageanalysis, dynamika, 2 page color brochure. Downloaded from http://www.imageanalysis.org.uk/what-we-do. Accessed on Feb. 9, 2015.
Imageanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#!products-services/ctnu. Accessed on Feb. 9, 2015.
Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.
Intelerad, InteleViewer, 2 page color brochure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQube%20one-sheet.pdf. Accessed on Feb. 9, 2015.
Kuhl, Helen: Comparison Chart/PACS, Customers Are Happy, But Looking for More, (color) Imaging Techology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
LUMEDX Cardiovascular Information System, CardioPACS, one page in color printout. Accessed at http://www.lumedx..com/pacs.aspx. Accessed on Feb. 9, 2015.
McKesson Enterprise Medical Imagining and PACS | McKesson, 1 page (color) printout. Accessed at http://www.mckesson.com/providers/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.
Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.
NOVARAD Enterprise Imaging Solutions, NOVAPACS, 2 page (color) printout. Accessed at http://ww1.novarad.net/novapacs. Accessed on Feb. 9, 2015.
PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/products_01.html. Accessed on Feb. 9, 2015.
PHILIPS IntelliSpace PACS, in 2 color page printout. Accessed at https://www.healthcare.philips.com/main/products/healthcare_informatics/products/enterprise_imaging_informatics/isite_pacs. Accessed on Feb. 9, 2015.
RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overview. Accessed on Feb. 9, 2015.
Sage Intergy PACS | Product Summary. Enhancing Your Workflow by Delivering Web-based Diagnostic Images When and Where You Need Them, in 2 color pages. (IRV-SS-INTPACS-PSS-031309). © 2009 Sage Software Healcare, Inc. Downloaded from http://www.greenwayhealth.com/solutions/intergy/. Accessed on Feb. 9, 2015.
Schellingerhout, Dawid, MD, et al.: "Coregistration of Head CT Comparison Studies: Assessment of Clinical Utility," Acad Radiol 2003; 10:242-248.
ScImage, Cardiology PACS, in 8 color page printout. Accessed at http://www.scimage.com/solutions/clinical-solutions/cardiology. Accessed on Feb. 9, 2015.
Sectra RIS PACS, in 2 color page printout. Accessed at https://www.sectra.com/medical/diagnostic_imaging/solutions/ris-pacs/. Accessed on Feb. 9, 2015.
Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.
Stryker, OfficePACS Power—Digital Imaging, 8 page color brochure, (MPP-022 Rev 4 BC/MP 300 1/07). © 2007 Stryker. Downloaded from http://www.stryker.com/emea/Solutions/Imaging/OfficePACSPowerDigitalImaging/ssLINK/emea/1557/022268. Accessed on Feb. 9, 2015.
UltraRAD—ultra VISION, 1 page (color). Downloaded from http://www.ultraradcorp.com/pdf/UltraVISION.pdf. Accessed on Feb. 9, 2015.
VioStream for VitreaView, 2 color pages printout. Accessed at http://www.vitalimages.com/solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2015.
VIZTEK Radiology PACS Software Vixtek Opal-RAD, 4 color page printout. Accessed at http://viztek.net/products/opal-rad. Accessed on Feb. 9, 2015.
Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.
Voyager Imaging—Voyager PACS, 3 page color brochure. Downloaded from http://www.intellirad.com.au/index.php/assets/Uploads/Voyager-Pacs3.pdf. Accessed on Feb. 9, 2015.
Tahmoush, D. and Samet, H., A New Database for Medical Images and Information, 2007, Medical Imaging 2007; PACS and Imaging Informatics, vol. 6516. pp. 1-7.
Ivetic, D. and Dragan, D., Medical Image on the Go!, 2009, J Med Syst, vol. 35, pp. 499-516.
Interview Summary dated May 1, 2015 in U.S. Appl. No. 14/095,123.
Final Office Action, dated Jun. 17, 2015 in U.S. Appl. No. 14/298,806.
Interview Summary dated Jun. 11, 2015 in U.S. Appl. No. 13/768,765.
Corrected Notice of Allowance, dated May 21, 2015 in U.S. Appl. No. 13/572,547.
Notice of Allowance dated Jul. 20, 2011, in U.S. Appl. No. 12/702,976.
Office Action dated Dec. 1, 2011, in U.S. Appl. No. 13/228,349.
Notice of Allowance dated Feb. 6, 2012, in U.S. Appl. No. 13/228,349.
Notice of Allowance dated Jul. 20, 2012, in U.S. Appl. No. 13/228,349.
Interview Summary dated Mar. 14, 2014, in U.S. Appl. No. 13/477,853.
Notice of Allowance dated May 17, 2010, in U.S. Appl. No. 11/268,261.
Supplemental Notice of Allowance dated Aug. 6, 2010, in U.S. Appl. No. 11/268,261.

(56) References Cited

OTHER PUBLICATIONS

Issue Notice dated Sep. 1, 2010, in U.S. Appl. No. 11/268,261.
Office Action dated May 16, 2011, in U.S. Appl. No. 12/857,915.
Interview Summary dated Sep. 6, 2011, in U.S. Appl. No. 12/857,915.
Final Office Action dated Dec. 15, 2011, in U.S. Appl. No. 12/857,915.
Office Action dated Jun. 12, 2012, in U.S. Appl. No. 12/857,915.
Office Action dated Aug. 23, 2013, in U.S. Appl. No. 12/857,915.
U.S. Appl. No. 14/687,853, filed Apr. 15, 2015, Reicher.
Interview Summary dated Feb. 4, 2014, in U.S. Appl. No. 12/857,915.
Notice of Allowance dated May 26, 2011 in U.S. Appl. No. 11/265,979.
Office Action dated Jun. 8, 2012 in U.S. Appl. No. 13/171,081.
Interview Summary dated Jul. 31, 2012 in U.S. Appl. No. 13/171,081.
Final Office Action dated Oct. 12, 2012 in U.S. Appl. No. 13/171,081.
Interview Summary dated Nov. 6, 2012 in U.S. Appl. No. 13/171,081.
Notice of Allowance, dated Sep. 4, 2013, in U.S. Appl. No. 13/171,081.
Non-Final Office Action dated Jan. 11, 2012 in U.S. Appl. No. 13/079,597.
Notice of Allowance dated Apr. 25, 2012, in U.S. Appl. No. 13/079,597.
Non-Final Office Action dated Apr. 4, 2013 in U.S. Appl. No. 13/535,758.
Notice of Allowance dated Aug. 23, 2013 in U.S. Appl. No. 13/535,758.
Non-Final Office Action dated May 5, 2011 in U.S. Appl. No. 12/870,645.
Non-Final Office Action dated May 31, 2013 in U.S. Appl. No. 13/345,606.
Interview Summary dated Aug. 15, 2013, in U.S. Appl. No. 13/345,606.
Notice of Allowance, dated Jan. 9, 2014, in U.S. Appl. No. 13/345,606.
Non Final Office Action Dated Nov. 10, 2011 in U.S. Appl. No. 13/118,085.
Interview Summary, dated Feb. 17, 2012, in U.S. Appl. No. 13/118,085.
Final Office Action, dated Apr. 13, 2012, in U.S. Appl. No. 13/118,085.
Notice of Allowance, dated Feb. 6, 2013, in U.S. Appl. No. 13/118,085.
Non Final Office Action dated Aug. 23, 2013 in U.S. Appl. No. 13/907,128.
Final Office Action dated Oct. 9, 2013 in U.S. Appl. No. 13/907,128.
Interview Summary dated Nov. 22, 2013 in U.S. Appl. No. 13/907,128.
Notice of Allowance dated Jan. 31, 2014 in U.S. Appl. No. 13/907,128.
Office Action, dated Dec. 29, 2014 in U.S. Appl. No. 14/298,806.
Interview Summary, dated Mar. 2, 2015 in U.S. Appl. No. 14/298,806.
Office Action, dated Mar. 13, 2014 in U.S. Appl. No. 11/942,687.
Interview Summary dated Jun. 28, 2012 in U.S. Appl. No. 11/944,027.
Final Office Action dated Oct. 22, 2012 in U.S. Appl. No. 11/944,027.
Notice of Allowance dated Jun. 5, 2013 in U.S. Appl. No. 11/944,027.
Interview Summary dated Jun. 7, 2011 in U.S. Appl. No. 11/944,000.
Appeal Brief dated Mar. 4, 2013 in U.S. Appl. No. 11/944,000.
Examiners Answer dated Jun. 26, 2013 in U.S. Appl. No. 11/944,000.
Office Action dated Feb. 3, 2012 in U.S. Appl. No. 12/622,404.
Interview Summary dated May 8, 2012 in U.S. Appl. No. 12/622,404.
Final Office Action dated Aug. 6, 2012 in U.S. Appl. No. 12/622,404.
Notice of Allowance dated Oct. 15, 2012 in U.S. Appl. No. 12/622,404.
Office Action dated Mar. 4, 2013 in U.S. Appl. No. 12/891,543.
Interview Summary dated Apr. 5, 2013 in U.S. Appl. No. 12/891,543.
Notice of Allowance dated Nov. 14, 2013 in U.S. Appl. No. 12/891,543.
Intelerad, IntelePACS, 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.
Mendelson, et al., "Informatics in Radiology—Image Exchange: IHE and the Evolution of Image Sharing," RadioGraphics, Nov.-Dec. 2008, vol. 28, No. 7.
Philips, IntelliSpace: Multi-modality tumor tracking application versus manual PACS methods, A time study for Response Evaluation Criteria in Solid Tumors (RECIST). 2012, Koninklijke Philips Electronics N.V., in four pages.
US 7,801,341, 09/2010, Fram et al. (withdrawn)
US 8,208,705, 06/2012, Reicher et al. (withdrawn)

* cited by examiner

FIG. 4

External Exam Description

External Exam Description exam Description: HEAD CT WO

Modality: CT

Active Status: Active ▼

Link Exam Type

Exam Code: 57501

Modality: CT

Active Status: ACTIVE

DICOM Modality: CT

Exam Description: HEAD WO

Procedure: CT OF THE HEAD

Link...  OK  Cancel

FIG. 8

EXAM TYPE MAPPING

CROSS-REFERENCE TO RELATED APPLICATIONS

This application claims the benefit of priority under 35 U.S.C. §119(e) of U.S. Provisional Application No. 61/522,633, filed Aug. 11, 2011, the disclosure of which is hereby incorporated by reference in its entirety.

BACKGROUND

There is a need for innovations that increase the efficiency and accuracy of interpretation of medical imaging exams.

SUMMARY

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

In one embodiment, a method of matching medical exam types comprises determining an exam type of an exam, accessing, by a computing system having one or more computer processors, an exam type data structure comprising associations between respective master exam types and one or more exam types selectively used by various entities, such that a first master exam type is associated with a first plurality of exam types used by one or more entities and a second master exam type is associated with a second plurality of exam types used by one or more entities, determining whether the determined exam type matches any of the exam types in the exam type data structure, in response to determining that the determined exam type matches one of the first plurality of exam types, associating the exam with the first master exam type so that any rules associated with exams of the first master exam type are automatically selected for use on the exam, and in response to determining that the determined exam type matches one of the second plurality of exam types, associating the exam with the second master exam type so any rules associated with exams of the second master exam type are automatically selected for use on the exam. In one embodiment, the method further comprises updating the exam type of the exam to include the matched master exam type. In one embodiment, the method further comprises replacing the exam type of the exam with the matched master exam type. In one embodiment, the method further comprises, in response to receiving a request for information and/or portion of the exam, replacing the exam type of the exam with the original determined exam type prior to providing the requested information and/or portion of the exam. In one embodiment, the requested information comprises a medical report. In one embodiment, the request is from an entity that associated the exam with the determined exam type. In one embodiment, the rules associated with the first exam type or the second exam type include rules for display, arrangement of various types of items within an exam, transfer, security, or viewing rights, associated with the corresponding exam. In one embodiment, the method further comprises, in response to not matching the determined exam type to any of the exam types in the exam type data structure, prompting a user of the computing system to indicate an association between the determined exam type and one or more exam types in the exam type data structure. In one embodiment, the method further comprises storing the association between the determined exam type and one or more exam types in the exam type data structure provided by the user in the exam type data structure so that the association is usable in automatically updating exam types of other exams having the determined exam type.

In one embodiment, the determined exam type comprises one or more of an exam description associated with the exam and/or a modality of the exam. In one embodiment, the exam description is provided via an HL-7 message that includes text or coded values. In one embodiment, the determined exam type comprises encoded information. In one embodiment, the determined exam type is determined based on data extracted from text or coded values in a data field associated with the images of the exam. In one embodiment, the data field is included in one or more of a cardiovascular information system (CVIS) file, a Digital Imaging and Communications in Medicine (DICOM) file, or a Health Level 7 (HL-7) file associated with the exam.

In one embodiment, the determined exam type matches an exam type in the exam type data structure if the determined exam type and the exam type in the data structure include substantially identical information. In one embodiment, the substantially identical information comprises one or more character strings of the determined exam type and one or more character strings of the matching exam type in the exam type data structure. In one embodiment, the determined exam type is based on one or more of: exam type information, patient demographic information, placer numbers, filler numbers or other coded information.

In one embodiment, the method further comprises applying one or more matching rules to determine whether the determined exam type matches an exam type in the exam type data structure.

In one embodiment, method further comprises determining a confidence level indicating a degree of similarity between the determined exam type and the exam types of the exam type data structure to which the first exam type is compared, wherein the determined exam type matches a respective exam type in response to the confidence level for comparison of the exam type with the respective exam type being above a threshold level. In one embodiment, the threshold level is set based on an organization or user preference.

In one embodiment, the method is performed in response to receiving an exam order including the determined exam type and determining that the determined exam type doesn't match any exam types in the exam type data structure.

BRIEF DESCRIPTION OF THE DRAWINGS

FIG. 4 is another sample screen shot of information displayed on a monitor including, in this specific example, an Advanced Beneficiary Notice and a clinical report template.

FIG. 6 is a sample user interface that may be displayed to a user when a non-matching exam type is ordered, received, or otherwise accessed.

FIG. 7 illustrates a sample screenshot of a user interface that may be used to link a form with one or more of an exam type, insurance plan, acquisition site, or other link.

FIG. 8 illustrates a sample screenshot of a user interface that allows selection and/or viewing of an attribute indicating whether or not a particular form needs to be returned to the medical facility (e.g., after completion by a patient).

DETAILED DESCRIPTION

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

As used herein, the terms "viewer" and "user" are used interchangeably to describe an individual (or group of individuals) that interfaces with a computing device. Users may include, for example, doctors, radiologists, hospital staff, or other individuals involved in acquisition, analysis, storage, management, or other tasks related to medical images. In other embodiments, users may include any individuals or groups of individuals that generate, transmit, view, and/or otherwise work with images of any type. Any discussion herein of user preferences should be construed to also, or alternatively, include user group preferences, site preferences, system preferences, and/or default software preferences.

Depending on the embodiment, the methods described with reference to the flowcharts, as well as any other methods discussed herein, may include fewer or additional blocks and/or the blocks may be performed in a different order than is illustrated. Software code configured for execution on a computing device in order to perform the methods may be provided on a tangible computer readable medium, such as a compact disc, digital video disc, flash drive, hard drive, memory device or any other tangible medium. Such software code may be stored, partially or fully, on a memory of a computing device (e.g., RAM, ROM, etc.), such as the computing system 150 (see discussion of FIG. 1, below), and/or other computing devices illustrated in the figures, in order to perform the respective methods. For ease of explanation, the methods will be described herein as performed by the computing system 150, but the methods are not limited to performance by the computing system 150 and should be interpreted to include performance by any one or more of the computing devices noted herein and/or any other suitable computing device.

Montage Customizations

Figure 1:
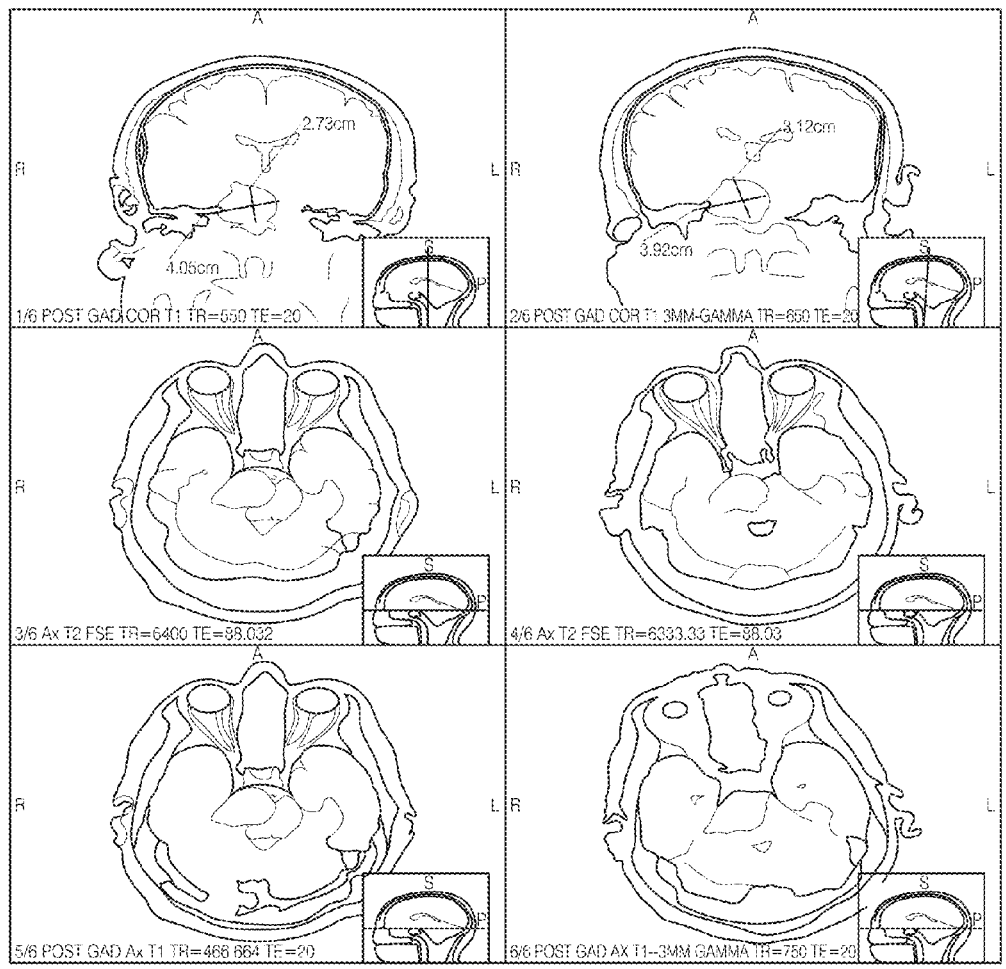
FIG. 1 is a sample montage that may be displayed on a computing device of a user, such as a radiologist or doctor.
Figure 2:
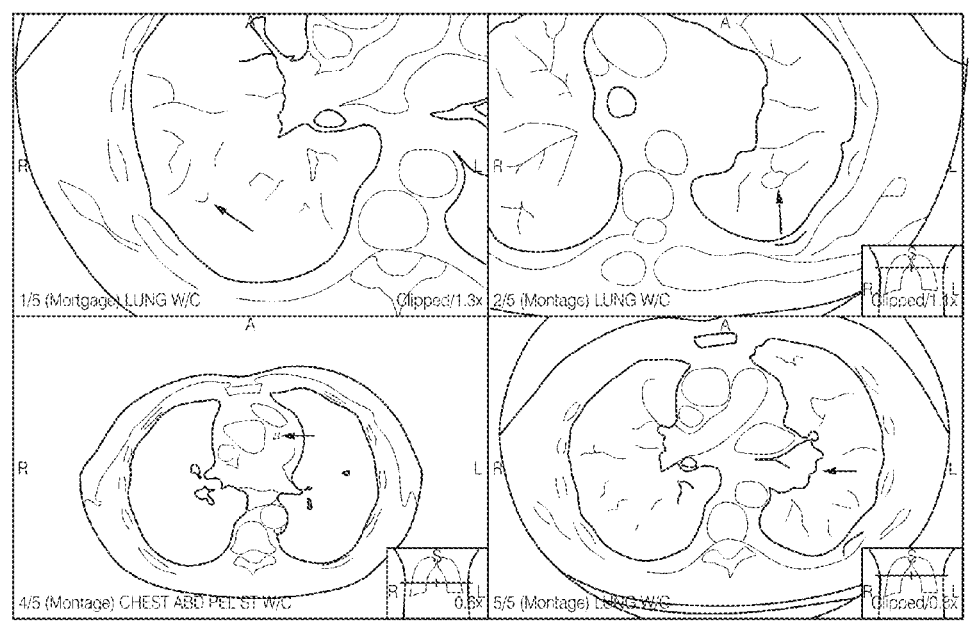
FIG. 2 is another example of a montage with a different number of images, including images that are formatted differently and include annotations (e.g., arrows pointing to areas of specific interest).

FIG. 1 is a sample montage that may be displayed on a computing device of a user, such as a radiologist or doctor. In the illustration of FIG. 1, the images of the montage are those selected by the reading physician as key images, such as at the time of review of an MRI of the Brain. The exam may include several image series, and hundreds or thousands of images. In one embodiment, the radiologist composes the montage by selecting one or more key images from one or more image series, and by adjusting various view settings of the images, such as window/level settings, centering, cropping, magnification, annotations, insets, etc. The same image might be selected more than once, but shown on the montage with different window/level settings, centering, cropping, magnification, annotations, insets, etc. FIG. 2 is another example of a montage with a different number of images, including images that are formatted differently and include annotations (e.g., arrows pointing to areas of specific interest).

In one embodiment, montages are saved as separate files, such as separate image files that are essentially a screenshot of a montage (e.g., a snapshot of the montages of FIG. 1 or 2). Thus, the montage that is configured by the viewer (e.g. radiologist or doctor) may be recalled at a later time. In one embodiment, the montage image file may be notated as a key image, such as according to the DICOM (Digital Imaging and Communications in Medicine) specification. The montage might include images from multiple examinations, or might include reference images such as illustrations or medical images exemplifying pathological or normal conditions.

In another embodiment, a montage having 1 or more images can be stored in one or multiple ways, including (1) storage of the complete composite montage image and/or (2) storage of sufficient information regarding each image so that the entire montage can be recreated upon future display or the individually stored images can be displayed, depending on the user's preferences, depending on the display environment (such as aspect ratio of the display window, monitor resolution, a combination of user preferences and display environment, or other factors.) For example, information regarding the arrangement of images in the montage, as well as information regarding display settings of respective images (e.g., magnification, brightness, centering, cropping, filters, annotations, insets, etc.) may be stored. This montage configuration or template information may then be recalled at a future time and used to re-build the montage. In this embodiment, storage of an image of the entire montage may not be necessary.

Additionally, other information related to the montage display/configuration may be stored (and later accessed to rebuild the montage or a montage of different images in the same configuration). For example, information regarding the device on which the montage was generated may be stored. In one embodiment, the resolution of the display device and/or size of a window in which the montage is created (e.g., horizontal pixels by vertical pixels) may be stored. Thus, the system (e.g., the device that will display the images and/or a device that is serving the images) may automatically select the format of the montage (such as 4×2 vs. 2×4) based on the aspect ratio of the images compared to the aspect ratio/orientation of the monitor. In another embodiment, the montage may be displayed in a manually sizable window, and the format of the montage may be automatically and optionally dynamically adjusted based on the aspect ratio of the window. In another embodiment, as images are added to the montage, the display format is automatically adjusted based on the aspect ratio of the montage window, the aspect ratio of the added images, and/or the number of images added.

Similarly, orientation of the display device (e.g., portrait or landscape), as well as matrix information (e.g., the number of rows and columns of images, e.g., 4 images×2 images or 6 images×4 images) may be stored in a montage template. Thus, multiple montage templates that include the same (or some of the same) images may be stored and selected based on characteristics of the computing device that later displays the montage, such as the display size. Accordingly, a first montage template may be automatically selected for viewing of images of a particular exam on a tablet computer while a second montage template may be automatically selected for viewing of images of the same particular exam on a desktop computer with a monitor having a much higher resolution. The computing device that displays the montage may automatically select the appropriate montage template, without any input from the user.

In one embodiment, the multiple images of a montage are simultaneously saved as key images (e.g., key DICOM objects) so that the images may be easily identified for inclusion in a montage that is generated based on a montage template.

As noted above, montage templates may be automatically selected based on the user, the display monitor (such as its resolution, aspect ratio, Smartphone vs PC monitor, etc), and/or other characteristics of an image viewing environment. Montage templates may be used to display the entire montage in the arrangement originally used by the viewer. In one embodiment, the user may cycle through other images of images series to which key images belong, keeping the same display characteristics as the key image as a default.

In another embodiment, an image may be one of many images in an image series, such as one axial image of a number of stacked axial images of the patient. In this case, in one embodiment, when an image is added to the montage the system may retain information related to the entire series of images so that a user may manipulate the montage image to also access other images in the same series.

By saving the key object information, a user can preserve the ability to manipulate each image individually, even when the images are displayed in the grouped montage mode.

Customized Display of Documents/Dialogs

Figure 3:
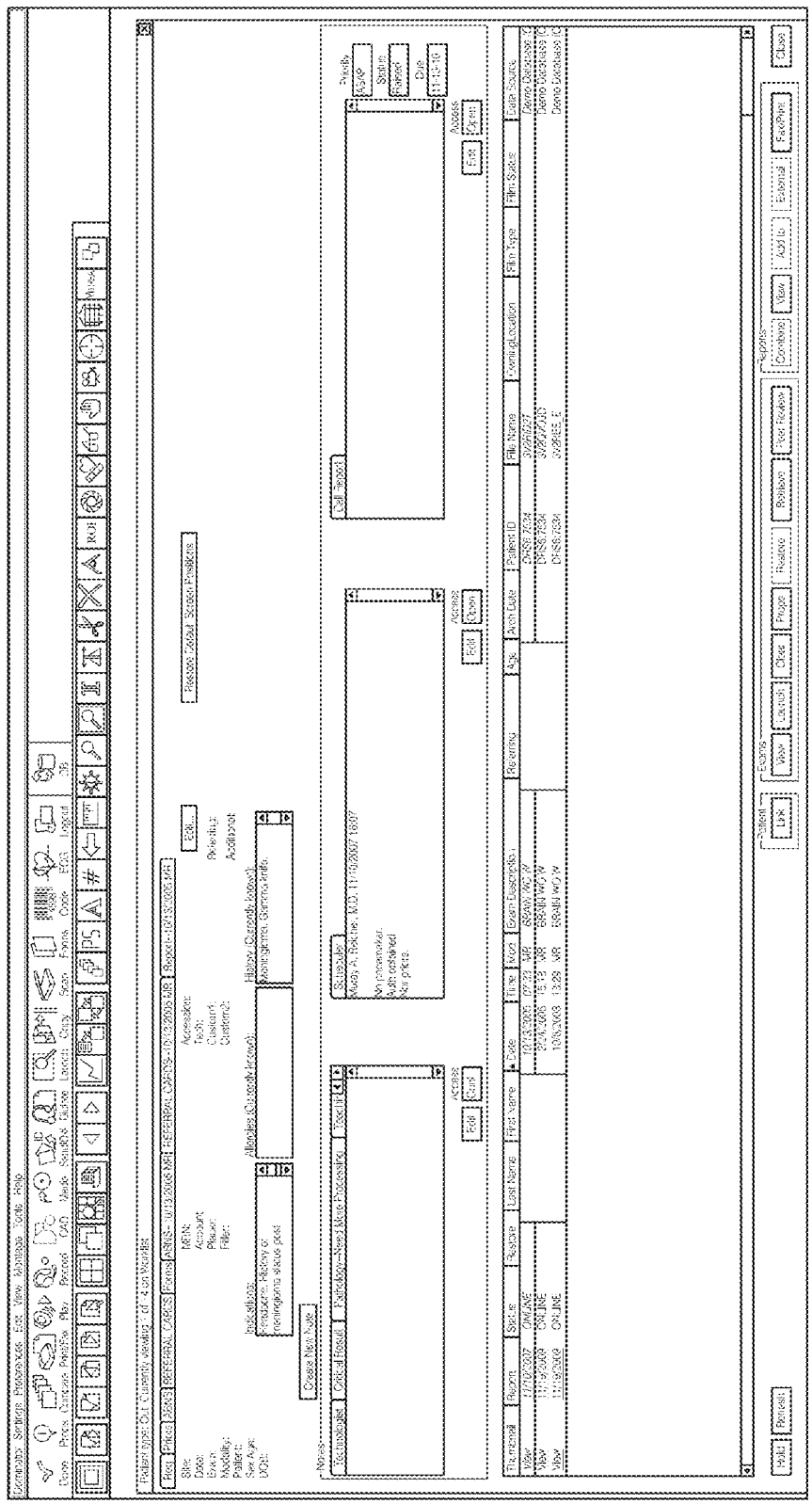
FIG. 3 is a sample screen shot of information displayed on a monitor by image viewing/manipulation software, such as DR Systems Unity RIS/PACS.
Figure 4:
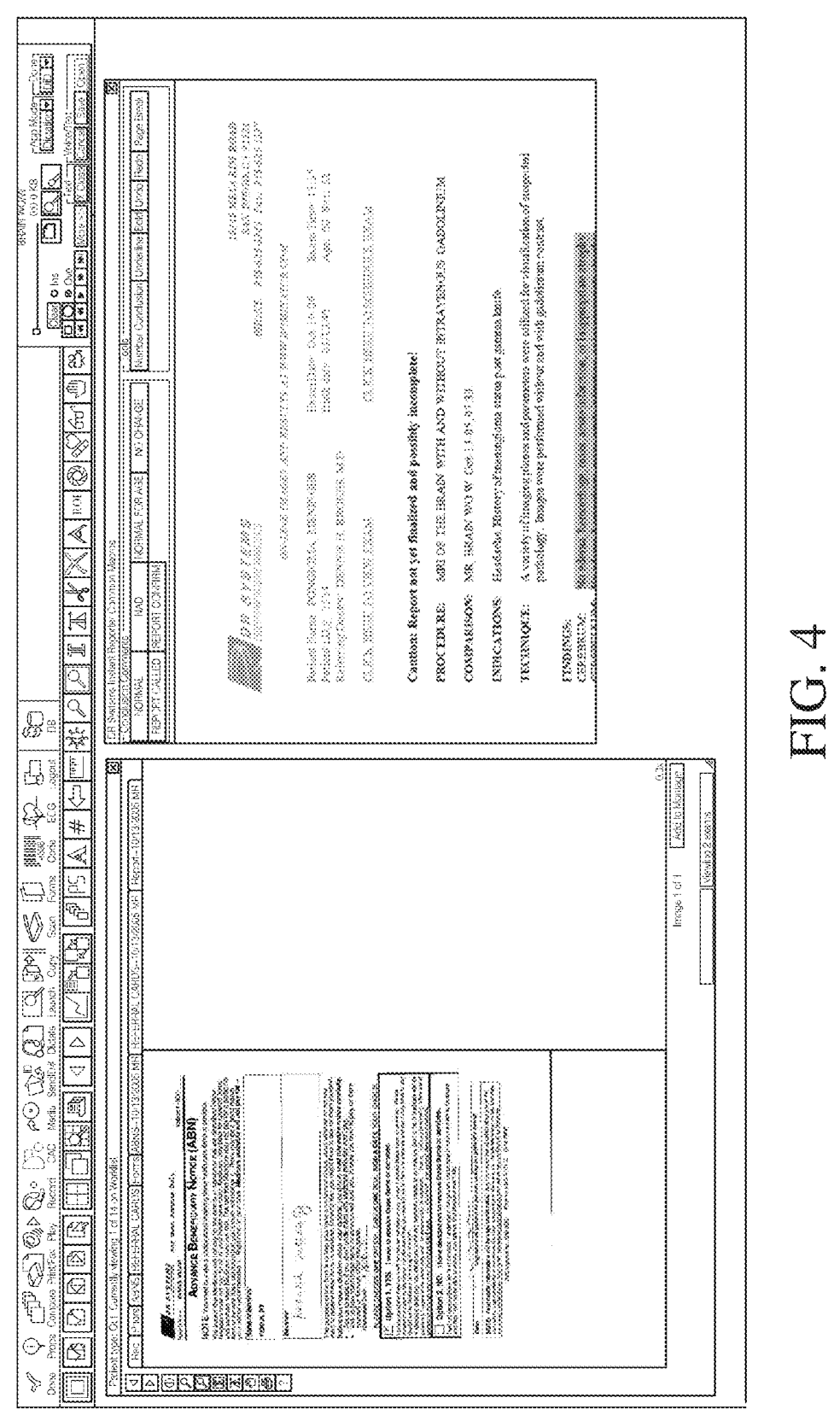

FIG. 3 is a sample screen shot of information displayed on a monitor by image viewing/manipulation software, such as DR Systems Unity RIS/PACS. The large dialog that fills most of the screen may be referred to as the Requisition, and it contains several tabs, some shown in red (the last three tabs) and others in blue (the first five tabs). Each tab represents a document or dialog associated with one or more imaging exams that are currently displayed on other monitors of a multi-monitor system. For example, FIG. 4 is a sample screen shot of one such arrangement, where the clinical report template associated with the current exam is displayed on the right, and a scanned document (Advanced Beneficiary Notice) is shown on the left.

In some scenarios, a reading physician may want to display the Requisition and the various available documents/dialogs/ webforms according to a preferred layout (e.g., a user-preferred layout), including size and position of various available elements. For example, with reference to FIG. 4, the user may have displayed the Advanced Beneficiary Notice by selecting one of the tabs from the upper left of the requisition, via another mouse action, keyboard shortcut or audio command, and also displayed the clinical report template through another means, such as a button click, mouse click, hotkey, or audio command. After selecting documents/dialogs for display, the user can adjust the size and position of these objects. Repeating these actions for other patients/exams is repetitive and not efficient. There can be many tabs available on the requisition or elsewhere for display of various categories of display objects, such as clinical reports, scanned documents, photographs, forms, prior exam lists etc.

In one advantageous embodiment, when a user sizes and positions a window, the system remembers that size and position for that category of object and for the user (or user group). The system may then automatically recreate that sizing and layout in the future for that user when a document of the category is displayed. Accordingly, each user can size and position these various documents/dialogs, and the system will remember the layout for any workstation across the network that uses a monitor of the same matrix size, while defaulting to a standard configuration for monitors of a different matrix size. In one embodiment, a single user may have multiple arrangements of documents/dialogs that are associated with different monitor sizes that are used by the user. In some embodiment, display settings may be stored for specific documents/dialogs as well, or as an alternative to the category settings discussed above.

In one embodiment, the display characteristics are associated with a display size (e.g., the matrix size and/or orientation of a monitor on which the document/dialog was viewed), such that the sizing and layout of documents of that category are displayed in that manner only when requested for viewing on the same or similar display configuration. In this embodiment, the system may select a default display layout for other monitor formats. If the user then sets the sizing and layout for another monitor format, the system will remember both set-ups for the user and make those layouts available to other devices throughout a network, such as a WAN or LAN. Any number of set-ups can be remembered.

Figure 5:
FIG. 5 illustrates a sample toolbox that may be used to select items for display on multiple monitors.

In one embodiment, the user can open a toolbox, such as the sample toolbox of FIG. 5, from any of multiple monitors by clicking a keyboard shortcut or mouse button, or via an audio command. This toolbox includes a list of all of the display objects available on the Requisition or other objects. The user can select any item on the list to immediately display the desired object, and the object will appear in the location associated with the users stored display layout preference or the default layout preference. Thus, the user does not need to drag a mouse to the monitor on which he wants to display the object, and one can control the display of an object on one monitor or in one display window, while working from another monitor or another display window. For example, a single monitor may be large enough to display many windows that might have previously required many monitors. In such an embodiment, the systems and methods discussed herein allow automatic positioning on the single monitor at a location associated with the user account. A reading physician who is viewing images on another monitor (or in another window of a same monitor) can thus control the display of objects on a first monitor without first dragging a mouse or distracting his vision to the first monitor. When the object appears, it follows the stored set-up instructions.

Exam Description Mapping

RIS, PACS, and other healthcare information systems typically contain a table of Exam Types, which is a list of various medical imaging exams available for selection. The Exam Type data structure (or "Exam type master file" or "Exam Type table") may include exam descriptions, modality descriptions, alphanumeric codes, as well as other information about each Exam Type—such as the default title of a clinical report based on that Exam Type, forms that should appear to the user (clerk, patient, technologist, and/or doctor) when that Exam Type is performed or viewed, linked clinical report templates, linked information about required supplies, clinical protocols, payment policies, charges, relative value/ productivity units, safety policies and more. In addition, various user or site preferences can be based on the Exam Type or modality, such as which exams should be automatically restored from archive for comparison when a particular Exam Type is scheduled or performed, which and how many exams are displayed for comparison when an exam is viewed, how a particular user prefers images to be displayed, and more. In addition, system automation may depend on the Exam Type data structure, such as rules automating the pre-fetching of prior comparison exams, reading physician protocols for exam display, automated creation of virtual series, keyboard shortcuts, reading sequences, routing of exams, and more. Therefore, in a sense, the Exam Type master file is a sort of DNA of some healthcare information system.

When a RIS/PACS or other related information system receives medical images or orders from external system, the Exam Type information may or may not match up with information already present in the Exam Type table. For example, exams of the same type may be named differently by different acquisition/viewing system. This information might be exchanged via information in a DR RIS, CVIS, DICOM metafile, in an HL-7 message, an order message, billing message, etc. In one embodiment, the system may offer configuration options that specify how the system should respond to a non-matching Exam Type, such as by either holding the processing of the message or exam import, or automatically adding the non-matching Exam Type to the Exam Type master file. However, either of these options prevents automated performance of actions that are customized for a particular exam type due to a non-matching Exam Type. In fact, setting up actions for a non-matching Exam Type often requires manual intervention. Alternatively, automatically adding a non-matching Exam Type to the Exam Type master file may disrupt automated steps that are dependent on a precisely linked and set-up list of Exam Types.

In order to make more efficient use of the Exam Type master file, in one embodiment an Exam Type mapping function is defined so that when a non-matching Exam Type is encountered by the system via the variety of different possible messages described above, the system prompts the user (in one or more of many possible manners—such as either a pop-up message, generation of a worklist, text-message of other means) that a non-matching Exam Type was encountered. The user can then map the non-matching Exam Type to the proper Exam Type from the master file, so that if the non-matching Exam Type is again encountered, it can be automatically processed (e.g., without any notification to the user). As a result, and depending on the type of in-bound message, the system might create a new scheduled exam with the internally mapped Exam Type, or import a DICOM imaging exam with the proper internally mapped Exam Type. All of the system automation that depends on the internally mapped Exam Type may then properly occur.

FIG. 6 is a sample user interface that may be displayed to a user when a non-matching Exam Type is ordered or received. In this embodiment, the Exam Description may be mapped to an Exam Type already stored in the Exam Type master file so that future exams having the same Exam Description are automatically mapped to the selected Exam Type and its corresponding actions.

In one embodiment, in addition to providing the ability to manually map Exam Types as discussed above, the system could apply rules that map Exam Types based on relative matching of character strings or other best match rules related to Exam Codes or other message characteristics. Based on a confidence level of a match, the automated mapping may be applied without further input from the user. For example, if a confidence level of a match is lower (e.g., below 80%) the user may be provided with the most likely matches and provided an opportunity to select from the short list of possible matches, rather than navigating through a list of all Exam Types in the master file.

In one embodiment, this mapping may be applied not only to inbound messages/exams, but also to outbound messages returning to external information systems, so that any edits, changes, and/or updates could be communicated back to the original system. For example, in one embodiment the exam type of an incoming exam may be changed to a master exam type from the exam type data structure, e.g., so that rules associated with the master exam type may be applied to the incoming exam. When the exam is transmitted elsewhere, such as back to the providing entity, the master exam type may not be recognized by the providing entity. Accordingly, in one embodiment, the exam type is reverted to the original exam time that was included in the recently received exam.

Depending on the embodiment, the exam type may include part or all of an exam description field, a coded value that references an exam type, an imaging modality, any other information, or combinations of information, associated with the exam.

In one embodiment, when an exam order is received via HL-7 or some other electronic interface, if the exam type that is ordered does not match the exam type data structure, the user is prompted to provide a mapping between the received exam type and one of the exam types in the exam type data structure. The provided mapping may then be stored for future automated linking when the exam type is received again in the future. Additionally, for a specific exam, if the exam type is linked or replaced, the system can remember the link and any associated data (such as the filler/placer or other values), and return that information to external systems (e.g., the original provider of the exam) along with any other data associated with the exam (e.g., a report associated with the exam).

Automated Forms to Patient Portal

Patient forms may be created and stored as form templates that are referred to in a data structure that links respective form templates with various links. The links can indicate when the forms are automatically presented and where they are automatically filed. For example, a particular form might be linked to a particular insurance, patient sex, patient language, age group, exam type, modality, or other stored information. As a result, when a scheduled exam is selected, the proper forms for that patient can be automatically presented for printing or electronic completion. In addition, the form templates can be linked to a specific naming convention and storage location. For example, one might create a CT Consent Form template and an MRI Consent Form template, and store information such that when either of these templates is used to create a CT Consent Form or MRI Consent Form, these forms are stored with the patient record such that they are labeled as Consent Forms, whereas there might be other form templates that would be stored as Insurance Forms, or Release Forms, etc.

Figure 7:
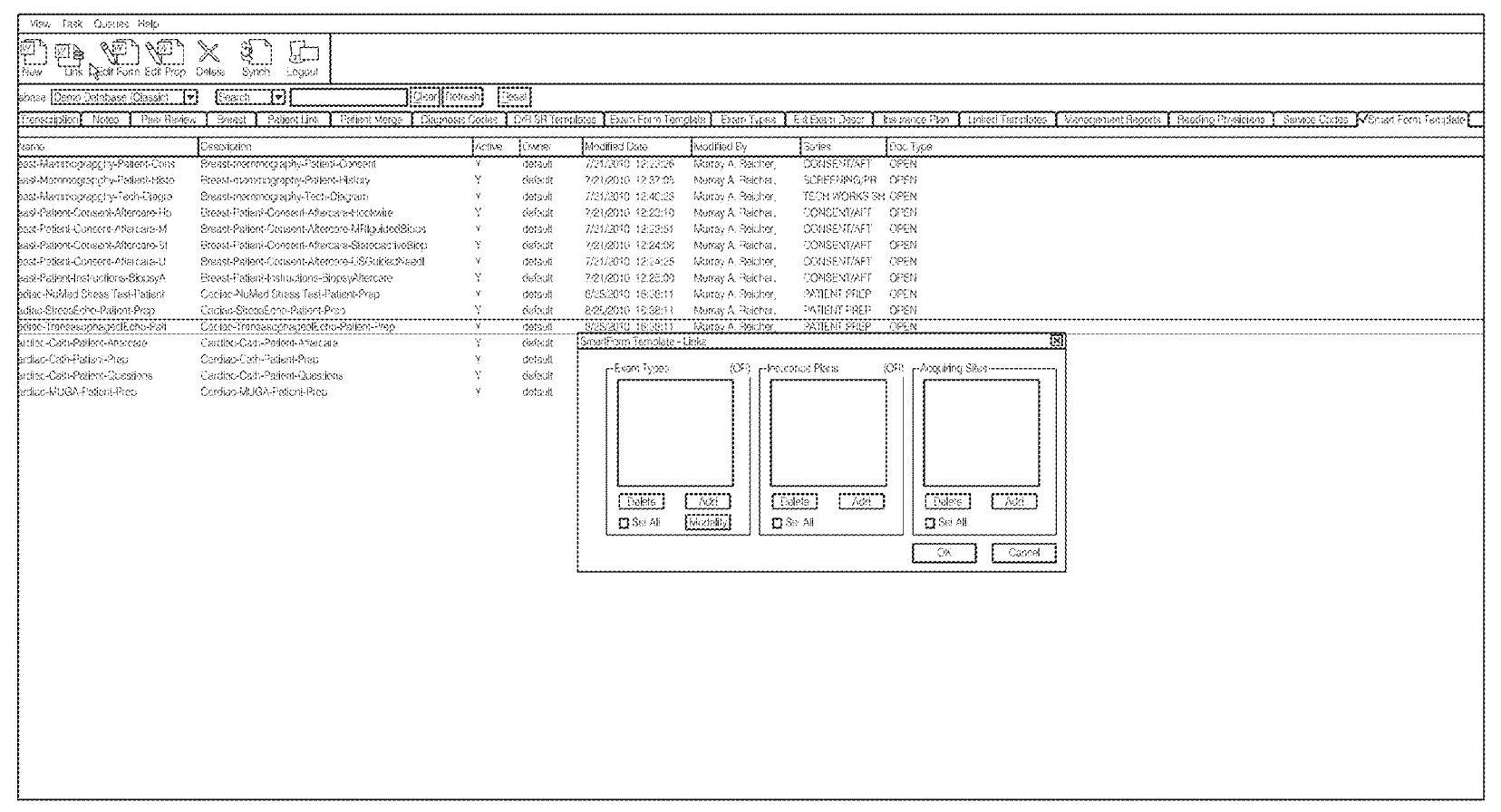

In one embodiment, when an exam is scheduled, the proper forms based on the automated links are posted to an internet-accessible location where the proper patient can view, print, or complete the forms. The forms may be automatically labeled with an identifying barcode, so that if the patient prints and completes the forms on paper, the paper can later be scanned, the bar code identified, and the form thus automatically filed with the proper patient, proper exam, and proper label. Each instance of a form may be provided with a specific identifier so that the information provided in the form (e.g., electronically or manually) may be associated with the proper patient's record and/or exam, and labeled properly. FIG. 7 illustrates a sample screenshot of a user interface that may be used to link a form with one or more of an Exam Type, Insurance Plan, Acquisition Site, or other link.

Figure 8:
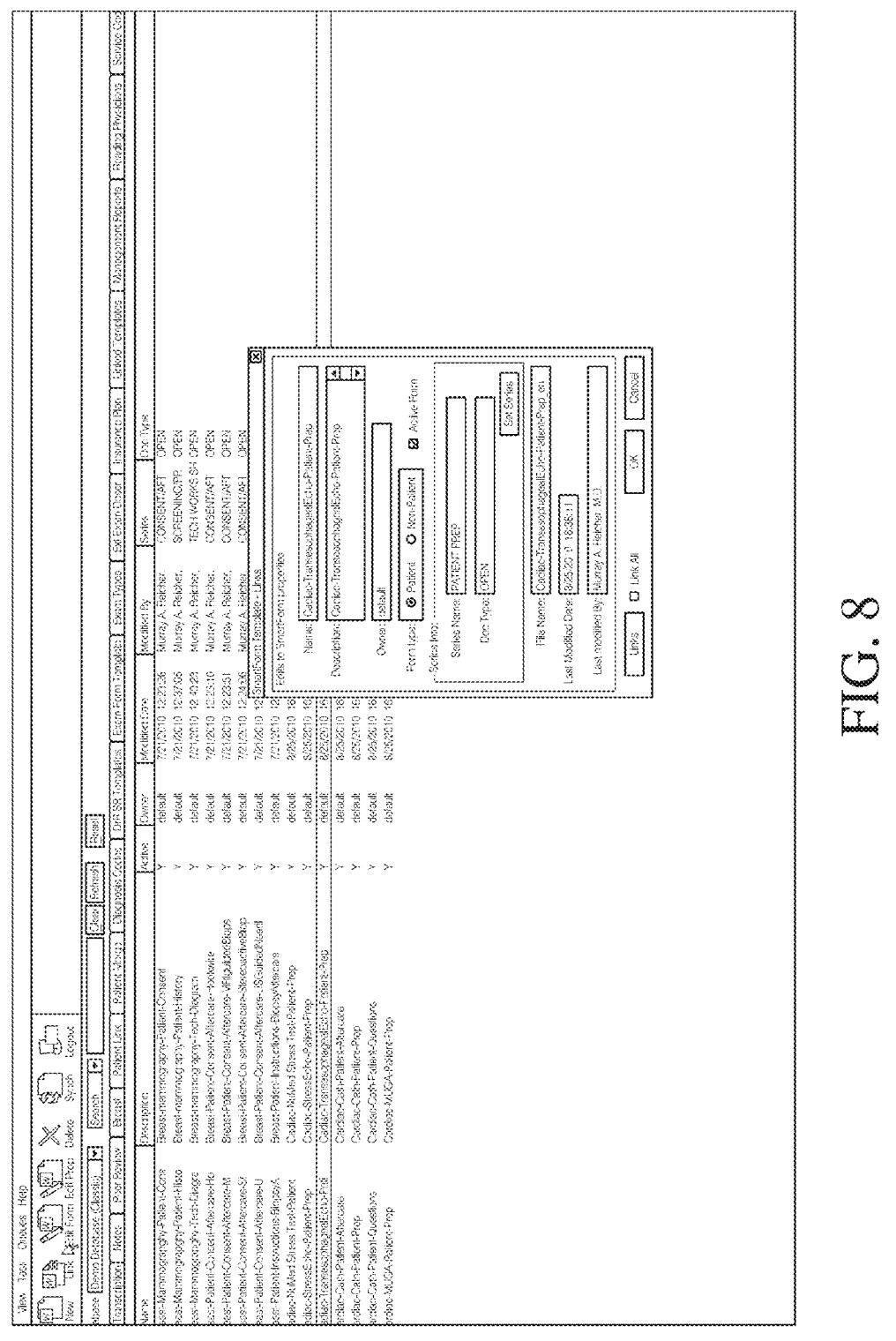

FIG. 8 is a screenshot of a sample user interface that may be accessible by a "Set Series" or similar button. The user interface allows the user to specify the category or series name that will be used to store instances of the form that are created using one of the templates stored in this list. Note that the templates might be one of many types of document formats, including MSWord, HTML, XML, CDA, CCR, etc. By placing a barcode on a printed form or by associating information with an electronic form, the system can automatically store the instance of the form with the proper patient, proper exam, and in the proper series. The series information may also further specify if, how, and when the form is presented for any particular user or by system default.

In one embodiment, forms may be associated with an attribute that indicates whether the form must be returned to system (e.g., to the medical facility that originally provided the form). Depending on various factors (e.g., reasons for visiting a medical facility), some quantity of forms provided to a patient may be for use of the patient (and/or a party other than the medical facility that provides the forms) and, thus, are not required to be returned to the medical facility. For example, a medical facility may not want forms that provide informational content to the patient returned to the medical facility. However, many forms provided to the patient may need to be returned to the medical facility and/or required to be returned prior to performance of an exam or procedure, for example. Thus, an attribute indicating whether or not a particular form needs to be returned to the medical facility may be indicated using a user interface similar to that shown in FIG. 8. A patient's file may then be automatically reviewed in order to determine if any forms that are required to be returned have not yet been returned (possibly a certain number of days after the forms are provided or a certain number of days before a scheduled exam).

Example System Implementation

Figure 9:
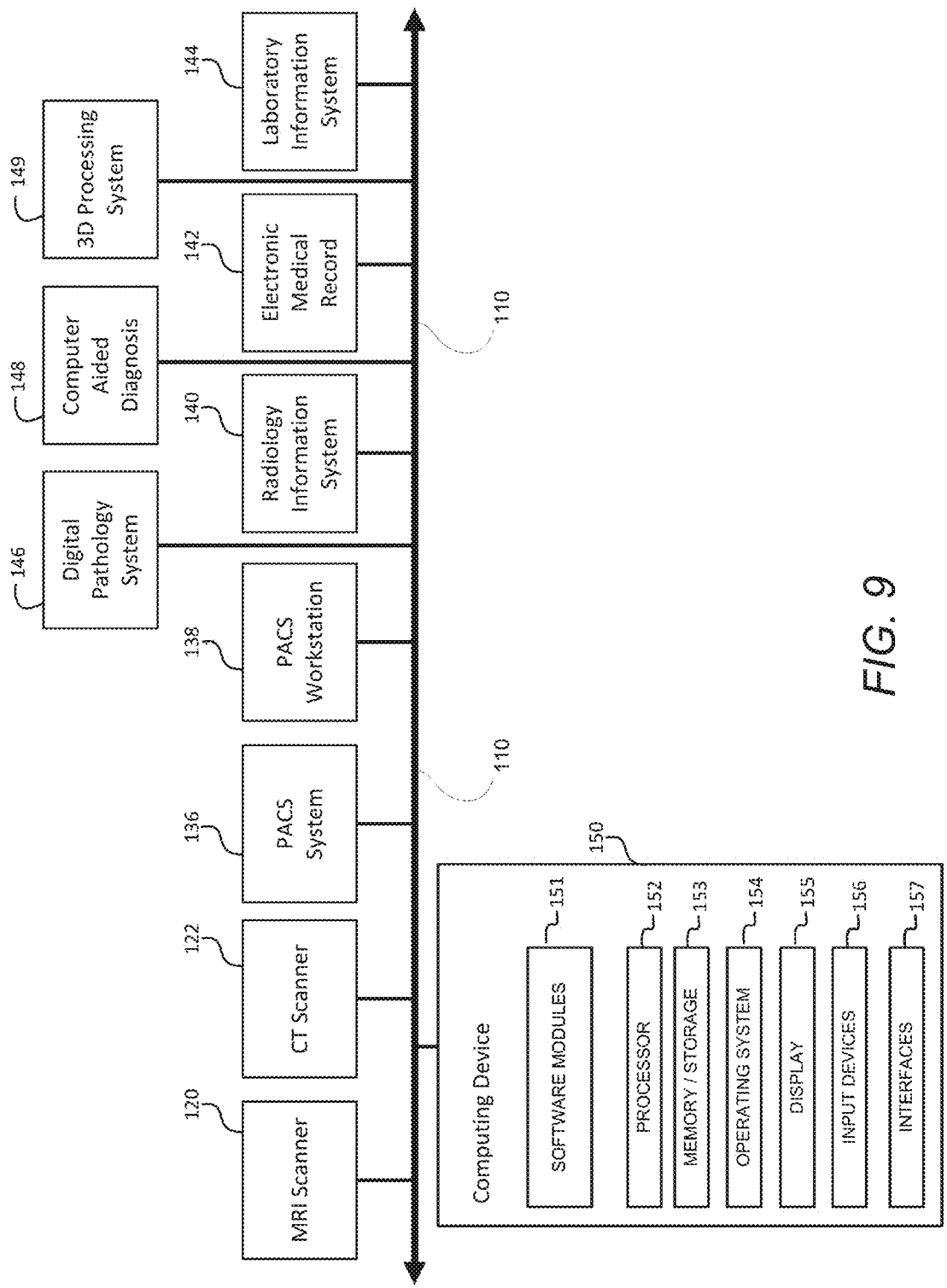
FIG. 9 is a system diagram which shows the various components of a system for performing the system and methods described above.

FIG. 9 is a system diagram which shows the various components of a system 100 for performing the system and methods described above, wherein the configuration of the system 100 may include fewer or additional features than are illustrated and individual components, such as the computing device 150, may also include fewer or additional components. In one embodiment the methods discussed above as being performed by "a system" are performed by the computing device 150. In other embodiments, the methods may be performed by any other suitable computing device.

The Computing Device 150 may take various forms. In one embodiment, the Computing Device 150 may be a computer workstation having software modules 151. In other embodiments, software modules 151 may reside on another computing device, such as a web server, and the user directly interacts with a second computing device that is connected to the web server via a computer network.

In one embodiment, the Computing Device 150 comprises a server, a desktop computer, a workstation, a laptop computer, a mobile computer, a Smartphone, a tablet computer, a cell phone, a personal digital assistant, a gaming system, a kiosk, an audio player, any other device that utilizes a graphical user interface, including office equipment, automobiles, airplane cockpits, household appliances, automated teller machines, self-service checkouts at stores, information and other kiosks, ticketing kiosks, vending machines, industrial equipment, and/or a television, for example.

The Computing Device 150 runs an operating system 154, such as an off-the-shelf operating system, for example, Windows, Linux, MacOS, Android, or iOS operation system. The Computing Device 150 may also run a more specialized operating system which may be designed for the specific tasks performed by the computing device 150.

The Computing Device 150 may include one or more computing processors 152. The computer processors 152 may include central processing units (CPUs), and may further include dedicated processors such as graphics processor chips, or other specialized processors. The processors generally are used to execute computer instructions based on the software modules 151 to cause the computing device to perform operations as specified by the modules 151. The modules 151 may include, by way of example, components, such as software components, object-oriented software components, class components and task components, processes, functions, attributes, procedures, subroutines, segments of program code, drivers, firmware, microcode, circuitry, data, data structures, data structures, tables, arrays, and variables. For example, modules may include software code written in a programming language, such as, for example, Java, JavaScript, ActionScript, Visual Basic, HTML, C, C++, or C#. While "modules" are generally discussed herein with reference to software, any modules may alternatively be represented in hardware or firmware. Generally, the modules described herein refer to logical modules that may be combined with other modules or divided into sub-modules despite their physical organization or storage.

The Computing Device 150 may also include memory 153. The memory 153 may include volatile data storage such as RAM or SDRAM. The memory 153 may also include more permanent forms of storage such as a hard disk drive, a flash disk, flash memory, a solid state drive, or some other type of non-volatile storage.

The Computing Device 150 may also include or be interfaced to one or more display devices 155 that provide information to the users. Display devices 155 may include a video display, such as one or more high-resolution computer monitors, or a display device integrated into or attached to a laptop computer, handheld computer, Smartphone, computer tablet device, or medical scanner. In other embodiments, the display device 155 may include an LCD, OLED, or other thin screen display surface, a monitor, television, projector, a display integrated into wearable glasses, or any other device that visually depicts user interfaces and data to viewers.

The Display Computing Device 150 may also include or be interfaced to one or more input devices 156 which receive input from users, such as a keyboard, trackball, mouse, 3D mouse, drawing tablet, joystick, game controller, touch screen (e.g., capacitive or resistive touch screen), touchpad, accelerometer, video camera and/or microphone.

The Computing Device 150 may also include one or more interfaces 157 which allow information exchange between Computing Device 150 and other computers and input/output devices using systems such as Ethernet, Wi-Fi, Bluetooth, as well as other wired and wireless data communications techniques.

The modules of Computing Device 150 may be connected using a standard based bus system. In different embodiments, the standard based bus system could be Peripheral Component Interconnect ("PCI"), PCI Express, Accelerated Graphics Port ("AGP"), Micro channel, Small Computer System Interface ("SCSI"), Industrial Standard Architecture ("ISA") and Extended ISA ("EISA") architectures, for example. In addition, the functionality provided for in the components and modules of Computing Device 150 may be combined into fewer components and modules or further separated into additional components and modules.

Computing Device 150 may communicate and/or interface with other systems and/or devices. In one or more embodiments, the computing device 150 may be connected to a computer network 110.

The computer network 110 may take various forms. It may be a wired network or a wireless network, or it may be some combination of both. The computer network 110 may be a single computer network, or it may be a combination or collection of different networks and network protocols. For example, the computer network 110 may include one or more local area networks (LAN), wide area networks (WAN), personal area networks (PAN), cellular or data networks, and/or the Internet.

Various devices and subsystems may be connected to the network 110. For example, one or more medical scanners may be connected, such as MRI scanners 120. The MRI scanners 120 may be used to acquire MRI images from patients, and may share the acquired images with other devices on the network 110. The network 110 may also be coupled to one or more CT scanners 122. The CT scanners 122 may also be used to acquire images and, like the MRI scanner 120, may then store those images and/or share those images with other devices via the network 110. Any other scanner or device capable of inputting or generating information could be included, including ultrasound, angiography, nuclear medicine, radiography, endoscopy, pathology, dermatology, etc.

Also connected to the network 110 may be a Picture Archiving and Communications System (PACS) 136 and PACS workstation 138. The PACS 136 is typically used for the storage, retrieval, distribution and presentation of images (such as those created and/or generated by the MRI scanner 120 and CT Scanner 122). The medical images may be stored in an independent format, an open source format, or some other proprietary format. A common format for image storage in the PACS system is the Digital Imaging and Communications in Medicine (DICOM) format. The stored images may be transmitted digitally via the PACS system, often reducing or eliminating the need for manually creating, filing, or transporting film jackets.

The network 110 may also be connected to a Radiology Information System (RIS) 140. The radiology information system 140 is typically a computerized data storage system that is used by radiology departments to store, manipulate and distribute patient radiological information such as Radiology Reports.

Also attached to the network 110 may be an Electronic Medical Record (EMR) system 142. The EMR system 142 may be configured to store and make accessible to a plurality of medical practitioners computerized medical records. Also attached to the network 110 may be a Laboratory Information System 144. Laboratory Information System 144 is typically a system which stores information created or generated by clinical laboratories. Also attached to the network 110 may be a Digital Pathology System 146 used to digitally manage and store information related to medical pathology.

Also attached to the network 110 may be a Computer Aided Diagnosis System (CAD) 148 used to analyze images. In one embodiment, the CAD 148 functionality may reside in a computing device separate from Information Display Computing Device 150 while in another embodiment the CAD 148 functionality may reside within Information Display Computing Device 150.

Also attached to the network 110 may be a 3D Processing System 149 used to perform computations on imaging information to create new views of the information, e.g., 3D volumetric display, Multiplanar Reconstruction (MPR) and Maximum Intensity Projection reconstruction (MIP). In one embodiment, the 3D Processing functionality may reside in a computing device separate from Information Display Computing Device 150 while in another embodiment the 3D Processing functionality may reside within Information Display Computing Device 150.

In other embodiments, other computing devices that store, provide, acquire, and/or otherwise manipulate medical data may also be coupled to the network 110 and may be in communication with one or more of the devices illustrated in FIG. 9, such as with the Information Display Computing Device 150.

As will be discussed herein, Computing Device 150 may be configured to interface with various networked computing devices in order to communicate medical information that is stored among the various systems present in the network. In other embodiments, Information Display Computing Device 150 may be used to display non-medical information.

Depending on the embodiment, the other devices illustrated in FIG. 9 may include some or all of the same components discussed above with reference to the Information Display Computer Device 150.

SUMMARY

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and partially or fully automated via, software code modules executed by one or more general purpose computers. For example, the methods described herein may be performed by an Information Display Computing Device and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of matching medical exam types, the method comprising:
   receiving, from an external computing device operated by a third party, electronic medical data of an exam associated with a particular patient;
   accessing, by a computing system having one or more computer processors, an exam type data structure, the exam type data structure storing associations between a list of master exam types and a list of received exam types;
   determining, by automated analysis of the electronic medical data by the computing system, an exam type of the received exam;
   determining, by the computing system, whether the determined exam type of the received exam matches any of the received exam types in the exam type data structure;
   in response to determining that the determined exam type of the received exam is associated with only one master exam type in the exam type data structure:
      associating, by the computing system, the received exam with the only one master exam type; and
      executing, by the computing system, one or more rules associated with the only one master exam type on the received exam; and
   in response to determining that the determined exam type of the received exam is not associated with any of the master exam types in the exam type data structure:
      determining, by automated analysis of the electronic medical data by the computing system, one of the master exam types that most closely matches the received exam type of the received exam;
      determining, by the computing system, a measure of confidence that the one of the master exam types corresponds to the received exam type of the received exam; and
      in response to determining, by the computing system, that the measure of confidence satisfies a predetermined threshold:
         associating, by the computing system, the received exam type of the received exam with the one of the master exam types;
         associating, by the computing system, the received exam with the one of the master exam types; and
         executing, by the computing system, one or more rules associated with the one of the master exam types on the received exam.

2. The method of claim 1, further comprising:
   further in response to determining that the determined exam type of the received exam is associated with only one master exam type in the exam type data structure:
      replacing the determined exam type of the received exam with the only one master exam type.

3. The method of claim 2, further comprising:
   in response to receiving, from another external computing device operated by another third party, a request for information and/or portion of the received exam, replacing an exam type of the received exam with the determined exam type of the received exam prior to providing the requested information and/or portion of the received exam.

4. The method of claim 3, wherein the another third party is the third party.

5. The method of claim 1, wherein the one or more rules associated with the only one master exam type or the one of the master exam types includes at least one of: rules for display, rules for arrangement of various types of items within an exam, rules for transfer, rules for security, or rules for viewing rights.

6. The method of claim 1, further comprising:
   in response to not matching the determined exam type of the received exam to any of the master exam types in the exam type data structure, prompting, by the computing system, a user of the computing system to indicate an association between the determined exam type of the received exam and one or more master exam types in the exam type data structure.

7. The method of claim 6, further comprising:
   storing, by the computing system, the association between the determined exam type of the received exam and the one or more master exam types in the exam type data structure provided by the user in the exam type data structure so that the association is usable in automatically updating exam types of other exams having the determined exam type.

8. The method of claim 1, wherein the determined exam type of the received exam comprises one or more of: an exam description associated with the received exam, or a modality of the received exam.

9. The method of claim 8, wherein the exam description is provided via an HL-7 message that includes text or coded values.

10. The method of claim 1, wherein the determined exam type of the received exam comprises encoded information.

11. The method of claim 1, wherein the determined exam type of the received exam is determined based on data extracted from text or coded values in a data field associated with images of the received exam.

12. The method of claim 11, wherein the data field is included in one or more of: a cardiovascular information system (CVIS) file, a Digital Imaging and Communications in Medicine (DICOM) file, or a Health Level 7 (HL-7) file associated with the exam.

13. The method of claim 1, wherein the determined exam type of the received exam matches a master exam type in the exam type data structure if the determined exam type of the received exam and the master exam type in the data structure include substantially identical information.

14. The method of claim 13, wherein the substantially identical information comprises one or more character strings of the determined exam type of the received exam and one or more character strings of the matching master exam type in the exam type data structure.

15. The method of claim 1, wherein determining, by the computing system, whether the determined exam type of the received exam matches any of the received exam types in the exam type data structure comprises:

applying, by the computing system, one or more matching rules to determine whether the determined exam type of the received exam matches a master exam type in the exam type data structure.

16. The method of claim 1, wherein the predetermined threshold is set based on an organization or user preference.

17. The method of claim 3, wherein the requested information comprises a medical report.

18. The method of claim 1, wherein the determined exam type of the received exam is comprises one or more of: exam type information, patient demographic information, placer numbers, filler numbers, or other coded information.

19. The method of claim 1, wherein the method is performed in response to receiving an exam order including the determined exam type and determining that the determined exam type doesn't match any exam types in the exam type data structure.

20. The method of claim 1 further comprising:
augmenting, by the computing system, the electronic medical data with data associated with the patient and stored in the computing system;
preparing, by the computing system, to transmit the augmented electronic medical data to another external computing device operated by another third party by:
determining, by reference to the exam type data structure and by the computing system, a received exam type associated with the another third party and corresponding to the matching master exam type or the one of the master exam types; and
associating, by the computing system, the determined received exam type with the augmented electronic medical data; and
transmitting, by the computing system, the augmented electronic medical data to the another external computing device operated by the another third party.

21. The method of claim 1 further comprising:
in response to determining, by the computing system, that the measure of confidence does not satisfy the predetermined threshold:
determining, by automated analysis of the electronic medical data by the computing system, at least one additional of the master exam types that closely matches the received exam type of the received exam after the one of the master exam types;
prompting, by the computing system, a user of the computing system to select a matching master exam type from the group consisting of: the one of the master exam types, and the at least one additional of the master exam types;
associating, by the computing system, the received exam type of the received exam with the selected matching master exam type;
associating, by the computing system, the received exam with the selected matching master exam type; and
executing, by the computing system, one or more rules associated with the selected matching master exam type on the received exam.

22. A non-transitory computer readable storage medium storing computer-executable instructions configured for execution by one or more hardware processors of a computer system to cause the computer system to:
receive, from an external computing device operated by a third party, electronic medical data of an exam associated with a particular patient;
access an exam type data structure, the exam type data structure storing associations between a list of master exam types and a list of received exam types;
determine, by automated analysis of the electronic medical data, an exam type of the received exam;
determine whether the determined exam type of the received exam matches any of the received exam types in the exam type data structure;
in response to determining that the determined exam type of the received exam is associated with only one master exam type in the exam type data structure:
associate the received exam with the only one master exam type; and
execute one or more rules associated with the only one master exam type on the received exam; and
in response to determining that the determined exam type of the received exam is not associated with any of the master exam types in the exam type data structure:
determine, by automated analysis of the electronic medical data, one of the master exam types that most closely matches the received exam type of the received exam;
determine a measure of confidence that the one of the master exam types corresponds to the received exam type of the received exam; and
in response to determining that the measure of confidence satisfies a predetermined threshold:
associate the received exam type of the received exam with the one of the master exam types;
associate the received exam with the one of the master exam types; and
execute one or more rules associated with the one of the master exam types on the received exam.

23. The non-transitory computer readable storage medium of claim 22, wherein the computer-executable instructions are configured for execution by one or more hardware processors of a computer system to further cause the computer system to:
augment the electronic medical data with data associated with the patient and stored in the computing system;
prepare to transmit the augmented electronic medical data to another external computing device operated by another third party by:
determine, by reference to the exam type data structure, a received exam type associated with the another third party and corresponding to the matching master exam type or the one of the master exam types; and
associate the determined received exam type with the augmented electronic medical data; and
transmit the augmented electronic medical data to the another external computing device operated by the another third party.

24. The non-transitory computer readable storage medium of claim 22, wherein the computer-executable instructions are configured for execution by one or more hardware processors of a computer system to further cause the computer system to:
in response to determining that the measure of confidence does not satisfy the predetermined threshold:
determine, by automated analysis of the electronic medical data, at least one additional of the master exam types that closely matches the received exam type of the received exam after the one of the master exam types;
prompt a user of the computing system to select a matching master exam type from the group consisting of: the one of the master exam types, and the at least one additional of the master exam types;
associate the received exam type of the received exam with the selected matching master exam type;

associate the received exam with the selected matching master exam type; and execute one or more rules associated with the selected matching master exam type on the received exam.

25. A computing system comprising:

one or more storage devices configured to store electronic software instructions; and one or more computer processors in communication with the one or more storage devices and configured to execute the stored electronic software instructions to cause the computing system to:

receive, from an external computing device operated by a third party, electronic medical data of an exam associated with a particular patient;

access an exam type data structure, the exam type data structure storing associations between a list of master exam types and a list of received exam types;

determine, by automated analysis of the electronic medical data, an exam type of the received exam;

determine whether the determined exam type of the received exam matches any of the received exam types in the exam type data structure;

in response to determining that the determined exam type of the received exam is associated with only one master exam type in the exam type data structure:

associate the received exam with the only one master exam type; and execute one or more rules associated with the only one master exam type on the received exam; and in response to determining that the determined exam type of the received exam is not associated with any of the master exam types in the exam type data structure:

determine, by automated analysis of the electronic medical data, one of the master exam types that most closely matches the received exam type of the received exam;

determine a measure of confidence that the one of the master exam types corresponds to the received exam type of the received exam; and in response to determining that the measure of confidence satisfies a predetermined threshold:

associate the received exam type of the received exam with the one of the master exam types;

associate the received exam with the one of the master exam types; and execute one or more rules associated with the one of the master exam types on the received exam.

26. The computing system of claim 25, wherein the one or more computer processors are configured to execute the stored electronic software instructions to further cause the computing system to:

augment the electronic medical data with data associated with the patient and stored in the computing system;

prepare to transmit the augmented electronic medical data to another external computing device operated by another third party by:

determine, by reference to the exam type data structure, a received exam type associated with the another third party and corresponding to the matching master exam type or the one of the master exam types; and associate the determined received exam type with the augmented electronic medical data; and transmit the augmented electronic medical data to the another external computing device operated by the another third party.

27. The computing system of claim 25, wherein the one or more computer processors are configured to execute the stored electronic software instructions to further cause the computing system to:

in response to determining that the measure of confidence does not satisfy the predetermined threshold:

determine, by automated analysis of the electronic medical data, at least one additional of the master exam types that closely matches the received exam type of the received exam after the one of the master exam types;

prompt a user of the computing system to select a matching master exam type from the group consisting of: the one of the master exam types, and the at least one additional of the master exam types;

associate the received exam type of the received exam with the selected matching master exam type;

associate the received exam with the selected matching master exam type; and execute one or more rules associated with the selected matching master exam type on the received exam.

* * * * *

UNITED STATES PATENT AND TRADEMARK OFFICE
CERTIFICATE OF CORRECTION

PATENT NO. : 9,092,727 B1  
APPLICATION NO. : 13/572552  
DATED : July 28, 2015  
INVENTOR(S) : Murray A. Reicher Page 1 of 1

It is certified that error appears in the above-identified patent and that said Letters Patent is hereby corrected as shown below:

On The Title Page

In column 2 (page 4, item 56) at line 1, Under Other Publications, change "Browers-based" to --Browsers-based--.

In column 1 (page 5, item 56) at line 6, Under Other Publications, change "12 page.," to --12 pages,--.

In column 1 (page 5, item 56) at line 23, Under Other Publications, change "Incoprorated." to --Incorporated.--.

In column 1 (page 5, item 56) at line 30, Under Other Publications, change "Techology" to --Technology--.

In column 2 (page 5, item 56) at line 4, Under Other Publications, change "Healcare," to --Healthcare,--.

In column 2 (page 5, item 56) at line 39, Under Other Publications, change "Vixtek" to --Viztek--.

In column 2 (page 6, item 56) at line 33, Under Other Publications, change "Incoprorated." to --Incorporated.--.

In The Specification

In column 3 at lines 59-61, Delete "include performance by any one or more of the computing devices noted herein and/or any other suitable computing device." and insert the same on Col. 3, Line 58, as the continuation of the same paragraph.

In The Claims

In column 14 at line 62, In Claim 14, change "matching master" to --master--.

Signed and Sealed this  
Eighth Day of March, 2016

Michelle K. Lee  
*Director of the United States Patent and Trademark Office*